US012558471B2

(12) United States Patent
Tessmer et al.

(10) Patent No.: US 12,558,471 B2
(45) Date of Patent: Feb. 24, 2026

(54) RETRIEVABLE ENDOVASCULAR IMPLANT FOR FISTULA CREATION AND MATURATION

(71) Applicant: C.R. BARD, INC., Franklin Lakes, NJ (US)

(72) Inventors: Alexander W. Tessmer, Phoenix, AZ (US); Andrzej J. Chanduszko, Chandler, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 379 days.

(21) Appl. No.: 18/023,025

(22) PCT Filed: Sep. 16, 2021

(86) PCT No.: PCT/US2021/050592
§ 371 (c)(1),
(2) Date: Feb. 24, 2023

(87) PCT Pub. No.: WO2022/060933
PCT Pub. Date: Mar. 24, 2022

(65) Prior Publication Data
US 2024/0009369 A1      Jan. 11, 2024

Related U.S. Application Data

(60) Provisional application No. 63/079,087, filed on Sep. 16, 2020.

(51) Int. Cl.
*A61M 1/36* (2006.01)
*A61M 39/02* (2006.01)

(52) U.S. Cl.
CPC ...... *A61M 1/3655* (2013.01); *A61M 39/0208* (2013.01); *A61M 2039/0223* (2013.01); *A61M 2205/0238* (2013.01)

(58) Field of Classification Search
CPC ............ A61M 1/3655; A61M 39/0208; A61M 2039/0223; A61M 2205/0238;
(Continued)

(56) References Cited

U.S. PATENT DOCUMENTS

| | | | |
|---|---|---|---|
| 6,464,665 B1 | 10/2002 | Heuser | |
| 8,100,936 B2 * | 1/2012 | McGuckin, Jr | ....... A61F 2/0105 |
| | | | 606/200 |
| 8,734,480 B2 * | 5/2014 | Snow | ...................... A61F 2/012 |
| | | | 606/200 |
| 10,456,239 B2 | 10/2019 | Yevzlin | |

(Continued)

FOREIGN PATENT DOCUMENTS

| | | |
|---|---|---|
| CN | 109700582 A | 5/2019 |
| JP | 2000-505316 A | 5/2000 |
| JP | 2019-506202 A | 3/2019 |

*Primary Examiner* — Nicholas J. Weiss
*Assistant Examiner* — Brandon W. Levy
(74) *Attorney, Agent, or Firm* — Dickinson Wright PLLC; Andrew D. Dorisio

(57) ABSTRACT

An endovascular implant for forming a fistula includes a body including a wall forming a lumen having a distal opening and a proximal opening. An anchor is coupled to a distal end of the body adjacent the distal opening. The anchor may include a first anchor extending from a first side of a distal end of the body, and a second, separate anchor may extending from a second side of the distal end of the body. A retriever may be coupled to a proximal end of the body adjacent the proximal opening.

20 Claims, 3 Drawing Sheets

(58) Field of Classification Search

Figure 1:
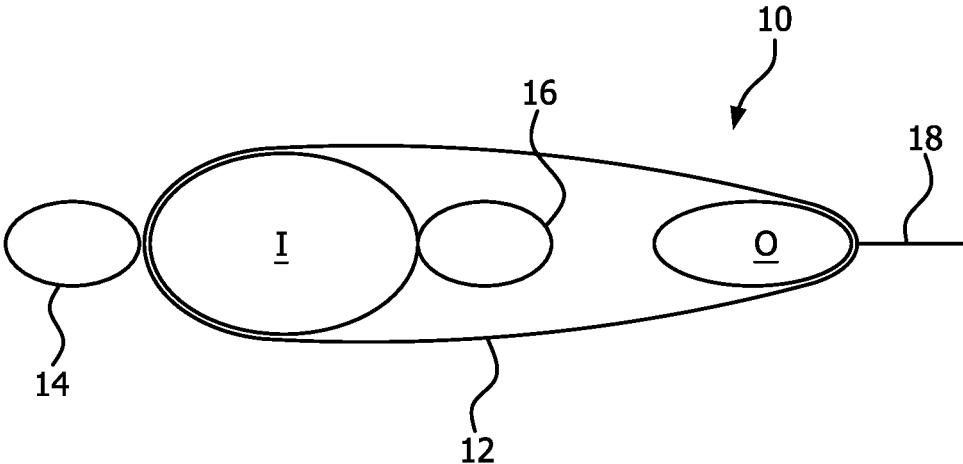

CPC .......... A61B 2017/00526; A61B 2017/00867; A61B 2017/00893; A61B 17/11; A61B 2017/1107; A61B 2017/1139; A61F 2/848; A61F 2002/8483; A61F 2002/8486; A61F 2/07; A61F 2/064; A61F 2/86; A61F 2/94; A61F 2/90; A61F 2/82; A61F 2/95; A61F 2002/9528; A61F 2210/0076; A61F 2230/0041; A61F 2/011; A61F 2002/016; A61F 2002/825; A61F 2/01; A61F 2250/0018; A61F 2220/0016; A61F 2230/0067; A61F 2/88

See application file for complete search history.

(56) References Cited

U.S. PATENT DOCUMENTS

| | | | |
|---|---|---|---|
| 2003/0040772 A1* | 2/2003 | Hyodoh .................... | A61F 2/90 |
| | | | 606/200 |
| 2003/0088256 A1 | 5/2003 | Conston | |
| 2005/0165441 A1 | 7/2005 | McGuckin, Jr. et al. | |
| 2006/0079930 A1* | 4/2006 | McGuckin ........... | A61F 2/0105 |
| | | | 606/200 |
| 2009/0105747 A1 | 4/2009 | Chanduszko et al. | |
| 2009/0287242 A1 | 11/2009 | Cartier et al. | |
| 2013/0158591 A1 | 6/2013 | Koehler et al. | |
| 2013/0226067 A1 | 8/2013 | Ward et al. | |
| 2014/0031842 A1 | 1/2014 | Brenneman et al. | |
| 2014/0088685 A1 | 3/2014 | Yevzlin et al. | |
| 2015/0157475 A1* | 6/2015 | Consigny .................. | A61F 2/94 |
| | | | 623/1.36 |
| 2017/0000939 A1 | 1/2017 | Cully et al. | |
| 2019/0015104 A1 | 1/2019 | Tuseth | |

* cited by examiner

RETRIEVABLE ENDOVASCULAR IMPLANT FOR FISTULA CREATION AND MATURATION

This application claims the benefit of U.S. Provisional Patent Application Ser. No. 63/079,087, filed Sep. 16, 2020. This application is related to U.S. Provisional Patent Application No. 62/787,985, filed on Jan. 3, 2019, and U.S. patent application Ser. No. 16/733,583, filed Jan. 3, 2020. The disclosures of each of these applications are incorporated herein by reference.

TECHNICAL FIELD

This disclosure pertains to medical apparatuses and, in particular, to a retrievable endovascular implant for fistula creation and maturation.

BACKGROUND

Currently, the only option for creation of an arteriovenous (AV) fistula in the United States for end-stage renal disease (ESRD) patients requiring dialysis is to undergo invasive surgery. It is estimated that just over 70,000 AV fistulas were created in 2016.

Fistula maturation is a process by which a fistula becomes suitable for cannulation and the criteria is the following: blood flow rate greater than 600 ml/min, diameter greater than 6 mm, depth less than 0.6 cm beneath skin and the aforementioned criteria should be met in 4-6 weeks after surgical creation. Fistula maturation continues to be a problem with approximately 50% of fistulas failing to mature. Possible reasons why fistulas fail to mature include inadequate dilation, accessory veins, stenosis, thrombosis, arterial/venous disease, and hypotension. Existing solutions include balloon angioplasty, obliteration of competing vessels, and biodegradable magnesium stents.

Accordingly, a device is needed that assists in maturing fistulas, expands the vessel providing adequate dilation, increases flow rate, and helps prevent stenosis. The device would allow for a physician to create an AV fistula, regardless of the distance between the vein and artery, via a percutaneous, minimally invasive technique that will greatly reduce vessel trauma from surgery, remove variability limiting the frequency of re-interventions, achieve better maturation success, and present more anatomical fistula options.

SUMMARY

According to a first aspect of the disclosure, an endovascular implant for forming a fistula is disclosed. The implant comprises a body including a wall forming a lumen, the body including a distal end having a distal opening and a proximal end having a proximal opening. The implant further comprises an anchor coupled to a distal end of the body adjacent the distal opening, the anchor including a first anchor extending from a first side of a distal end of the body, and a second anchor extending from a second side of the distal end of the body, the second anchor separated from the first anchor.

In one embodiment, the first and second anchors are separated by an inlet to the lumen. The implant may further include a retriever. The wall of the implant may comprise a material having a thickness, and further having a pair of interconnected hooks forming the retriever. Each hook of the pair of hooks includes a first longitudinal portion extending from and unitarily formed with the wall and a second portion connected to the first longitudinal portion, the second portions of the interconnected hooks, each hook being formed of the material of the wall having the thickness.

In one embodiment, the pair of hooks are at least partially connected together by a bond. The bond may comprise a weld.

The pair of interconnected hooks may include a radially innermost portion offset from a central axis of the body. The first longitudinal portion of each hook may be partially twisted and the second portion projects radially inward from the first longitudinal portion.

According to a further aspect of the disclosure, an endovascular implant for forming a fistula is provided. The implant comprises a body including a wall forming a lumen. The body includes a distal end having a distal opening and a proximal end having a proximal opening. An anchor is coupled to the distal end of the body adjacent the distal opening, and a retriever is coupled to the proximal end of the body adjacent the proximal opening.

In one embodiment, the wall comprises a material having a thickness. The implant may further include a pair of interconnected hooks forming the retriever. Each hook of the pair of hooks includes a first longitudinal portion extending from and unitarily formed with the wall and a second portion connected to the first longitudinal portion. The second portions of the interconnected hooks, each hook being formed of the material of the wall having the thickness.

In one embodiment, the pair of hooks are at least partially connected together by a bond, such as a weld. The pair of interconnected hooks may include a radially innermost portion offset from a central axis of the body. The first longitudinal portion of each hook may be partially twisted and the second portion may projects radially inward from the first longitudinal portion.

The body may comprise a mesh having a coating. The anchor may comprise first and second anchors separated by an inlet to the lumen.

According to a further aspect of the disclosure, an endovascular implant for forming a fistula is provided. The implant comprises a body including a wall forming a lumen, the body including a distal end having a distal opening and a proximal end having a proximal opening. An anchor is coupled to a distal end of the body adjacent the distal opening. The anchor includes a first anchor extending from a first side of a distal end of the body, and a second separate anchor extending from a second side of the distal end of the body. A retriever comprises a pair of interconnected hooks, each hook of the pair of hooks having a first longitudinal portion extending from and unitarily formed with the wall and a second portion connected to the first longitudinal portion, the second portions of the interconnected hooks, each hook being formed of the material of the wall having the thickness. The anchor may comprise first and second anchors separated by an inlet to the lumen In any of the foregoing embodiments, the body may comprise a mesh having a coating.

BRIEF DESCRIPTION OF THE DRAWING FIGURES

Figure 1A:
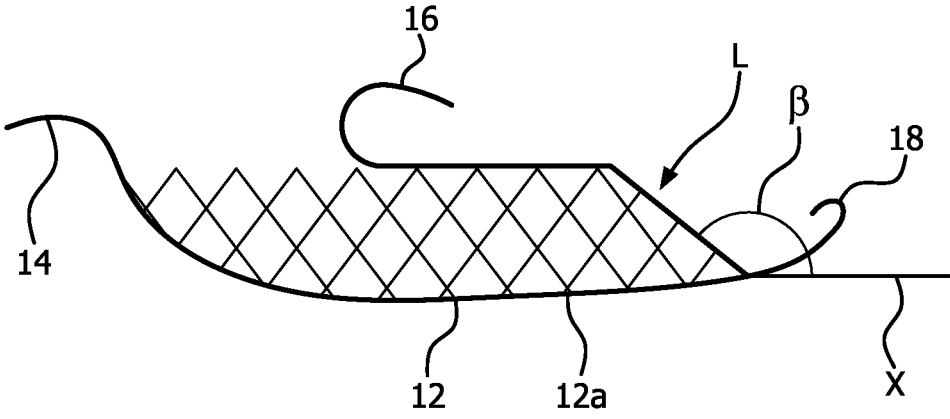
Figure 2:
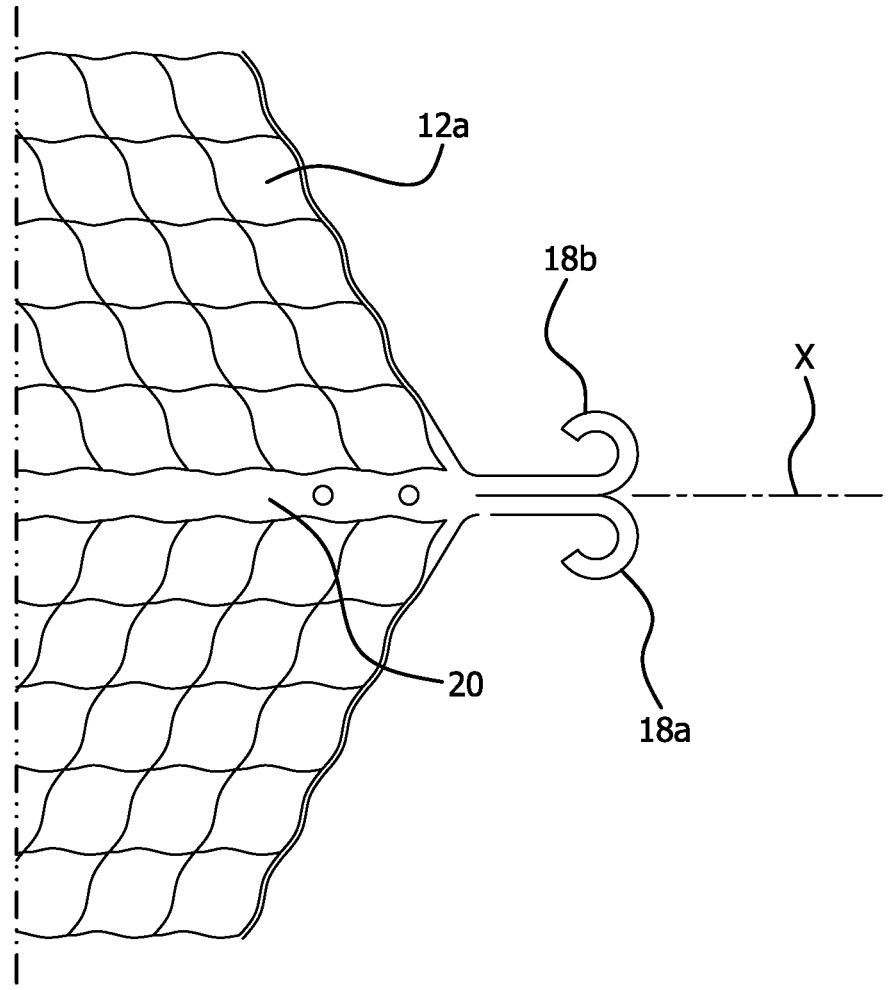
Figure 4:
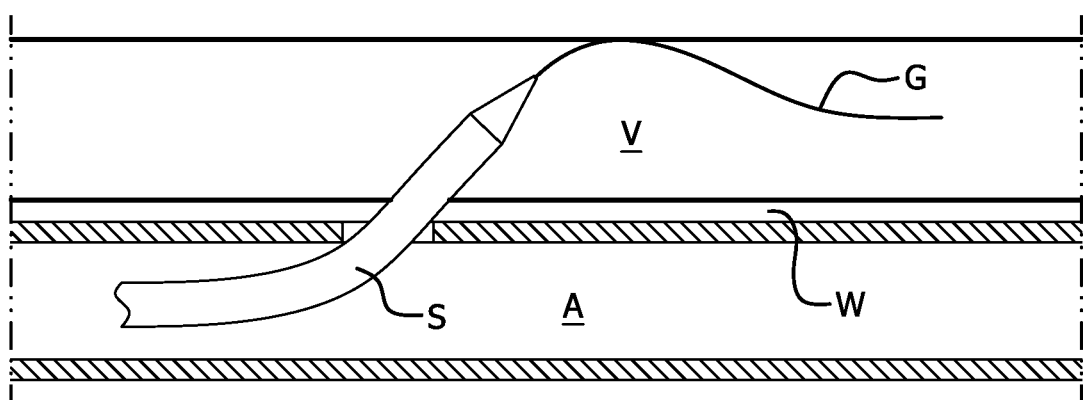
Figure 5:
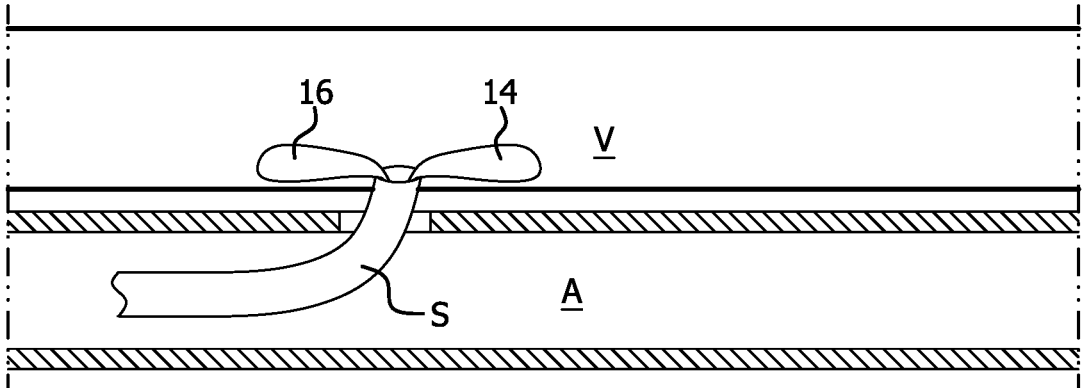
Figure 6:
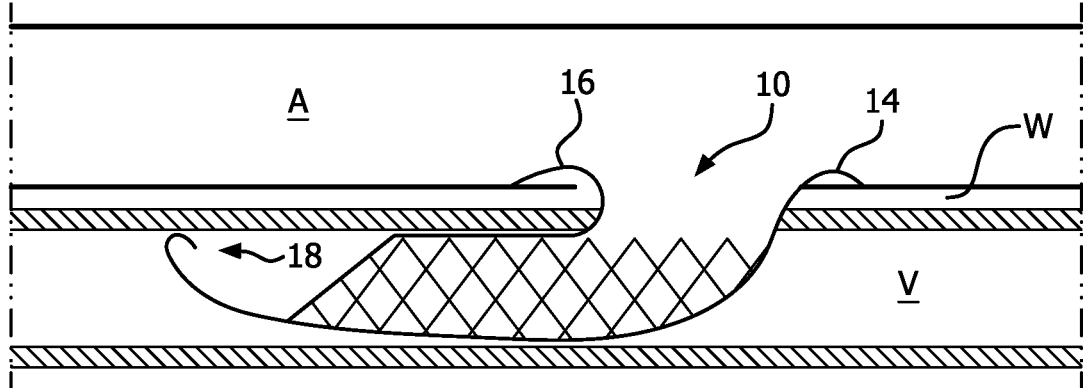

FIG. 1 is a top view of an implant according to one aspect of the disclosure;

FIG. 1*a* is a side sectional view of an implant of FIG. 1;

FIG. 2 is a top plan view of a precursory for forming the implant including a retriever; and FIGS. 4-6 are progressive schematic views illustrating a possible use of the implant to form a fistula.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Referring to the drawing figures, an implant 10 is provided for forming an AV fistula, which is shown from both the top (FIG. 1) and the side (FIG. 1*a*). In the illustrated embodiment, the implant 10 comprises a single piece of tubing forming a tubular body 12. As illustrated in FIG. 1*a*, the tubular body 12 may comprise a wall formed of a mesh comprising wires or struts defining a plurality of closed cells 12*a*, which thus provide the body with a significant degree of flexibility.

The body 12 may be at least partially covered by a coating or membrane formed of a biocompatible material (e.g., ePTFE, polyurethane, etc.). The covering may be self-sealing, such as after a needle puncture. As can be understood from FIGS. 1 and 1*a*, the so-coated body 12 thus forms a lumen L having a distal opening (inlet I) and a proximal opening (outlet O) for together passing a flow of fluid, such as blood, in an associated vessel once inserted therein, while also lending support for the corresponding vessel to maintain patency.

The implant 10 may further include one or more anchors 14, 16 for anchoring the implant in place in a desired location, such as to form an AV fistula. The anchors 14, 16 are shown on the distal end of the implant 10, which correspond to the arterial side at a fistula site. The anchors 14, 16 may be oval in shape, or may have different shapes, and may be close-ended or open-ended. The anchors 14, 16 may extend obliquely and in opposite directions from adjacent an open upper (inlet) end of the implant 10. While two anchors 14, 16 are shown, more than two may be provided. Anchors (not shown) may also optionally be provided on the proximal end of the implant 10, corresponding to the location in the vein in use.

The implant 10 may also include a retriever 18. In one embodiment, the retriever 18 takes the form of a hook, the details of which are outlined further in the following description. The hook forming the retriever 18 may be located adjacent a proximal (outlet O) end of the implant 10.

The hook forming the retriever 18 is connected to the body 12, such as directly to an elongated spine 20 extending longitudinally along one side (e.g., an underside) of the implant 10 in the illustrated orientation, and is bounded on both lateral sides by the closed cells 12*a*. This spine 20 is formed of material that is generally wider circumferentially than the wires or struts forming the closed cells 12*a* of the body 12, and thus enhances the ability of the implant 10 to be retrieved using the associated retriever 18. While only one spine 20 is shown, more than one may be present, if desired, or the spine may be omitted altogether.

Formation of the implant 10 may be achieved by cutting the body 12 from a single piece of tubular material. Turning to the plan view of FIG. 2, this processing allows for two longitudinally extending J-shaped hooks 18*a*, 18*b* to be cut directly from the single thickness material, which may be considered to create a preform for forming the implant 10 (and thus the hooks have a similar thickness to a wall of the body 12). A radially innermost portion of each hook 18*a*, 18*b* is offset from a central axis X of the body. The hooks 18*a*, 18*b* may thus be folded or bent/twisted into a juxtaposed, abutting relationship, and then bonded together (such as by a weld) to form a double thickness hook serving as the retriever 18 of FIGS. 1 and 1*a*. It can be appreciated that, in view of the forming process described above, the height of the hooks 18*a*, 18*b* may be substantially smaller in relation to the diameter of the body 12 of the implant 10, thus minimizing impedance to fluid flow.

Turning now to FIGS. 3-5, use of the implant 10 to form an AV fistula is described. A sheath S may be used to deliver the implant, such as by delivering the sheath to a fistula creation site through a vein V and a needle (not shown) may be used to create (puncture) a hole through the venous and the arterial wall W. A guidewire G is then used to cross into the artery A through the needle.

The implant 10 may then be delivered to the tip of the sheath S. The sheath S is then retracted. Consequently, the distal anchors 14, 16 of the implant 10 are deployed, followed by the tubular body 12.

As a result, the lumen L provides a conduit for the arterial blood to flow into the vein, thus creating an AV fistula. Optionally, the vein V may be dilated with a PTA balloon prior to implantation to roughly match the implant diameter. The balloon may also be used to dilate the conduit created with the needle and the sheath prior to implantation or dilate the implant after its deployment.

After a particular time (e.g., several days or weeks), the implant 10 may be percutaneously removed. This may be done using a snare (not shown) to pull the implant longitudinally into a sheath. Turning back to FIG. 1*a*, it can also be understood that at least the end associated with the retriever 18 may be sloped or tapered so as to form a second angle with a horizontal axis X. As can be appreciated, when the retriever 18 is pulled longitudinally for purposes of retrieval, this taper allows for the narrower tapered portion of the implant 10 to initially enter the sheath when pulled toward the opening thereof. Further longitudinal movement into the sheath may thus cause a partial collapse of the implant 10 to ensure recovery, even if the inner diameter of the sheath is much smaller than the outer diameter of the implant 10.

The implant 10 may be made of a variety of materials. For example, the implant 10 may be fabricated from a shape memory material, such as Nitinol, or other metals/alloys, such as steel (e.g., stainless), nickel-chromium, cobalt-chromium alloys, titanium alloys, or the like. The implant 10 may also be formed of a polymer material, or even a bioabsorbable material, such as magnesium or other such materials, or composites of any materials.

The implant 10 may also be coated with a medicine or pharmacological agent (e.g., Paclitaxel) for treatment purposes, as is known in the art. The implant 10 may also be made radiopaque or incorporate radiopaque markers for identification using fluoroscopy.

Summarizing, this disclosure may be considered to relate to the following items:

1. An endovascular implant for forming a fistula, comprising:
  a body including a wall forming a lumen, the body including a distal end having a distal opening and a proximal end having a proximal opening; and an anchor coupled to a distal end of the body adjacent the distal opening, the anchor including a first anchor extending from a first side of a distal end of the body, and a second anchor extending from a second side of the distal end of the body, the second anchor separated from the first anchor.

2. The endovascular implant of item 1, wherein the first and second anchors are separated by an inlet to the lumen.

3. The endovascular implant of item 1 or item 2, further including a retriever.

4. The endovascular implant of any of items 1-3, wherein the wall comprises a material having a thickness, and further having a pair of interconnected hooks forming the retriever, each hook of the pair of hooks having a first longitudinal portion extending from and unitarily formed with the wall and a second portion connected to the first longitudinal portion, the second portions of the interconnected hooks, each hook being formed of the material of the wall having the thickness.

5. The endovascular implant of item 4, wherein the pair of hooks are at least partially connected together by a bond.

6. The endovascular implant of item 5, wherein the bond comprises a weld.

7. The endovascular implant of any of items 4-6, wherein the pair of interconnected hooks include a radially innermost portion offset from a central axis of the body.

8. The endovascular implant of any of items 4-7, wherein the first longitudinal portion of each hook is partially twisted and the second portion projects radially inward from the first longitudinal portion.

9. The endovascular implant of any of items 1-8, wherein the body comprises a mesh having a coating.

10. An endovascular implant for forming a fistula, comprising:
   a body including a wall forming a lumen, the body including a distal end having a distal opening and a proximal end having a proximal opening; and
   an anchor coupled to the distal end of the body adjacent the distal opening,
   a retriever coupled to the proximal end of the body adjacent the proximal opening.

11. The endovascular implant of item 10, wherein the wall comprises a material having a thickness, and further having a pair of interconnected hooks forming the retriever, each hook of the pair of hooks having a first longitudinal portion extending from and unitarily formed with the wall and a second portion connected to the first longitudinal portion, the second portions of the interconnected hooks, each hook being formed of the material of the wall having the thickness.

12. The endovascular implant of item 11, wherein the pair of hooks are at least partially connected together by a bond.

13. The endovascular implant of item 11, wherein the bond comprises a weld.

14. The endovascular implant of item 11, wherein the pair of interconnected hooks include a radially innermost portion offset from a central axis of the body.

15. The endovascular implant of item 11, wherein the first longitudinal portion of each hook is partially twisted and the second portion projects radially inward from the first longitudinal portion.

16. The endovascular implant of any of items 11-15, wherein the body comprises a mesh having a coating.

17. The endovascular implant of any of items 11-16, wherein the anchor comprises first and second anchors separated by an inlet to the lumen.

18. An endovascular implant for forming a fistula, comprising:
   a body including a wall forming a lumen, the body including a distal end having a distal opening and a proximal end having a proximal opening;
   an anchor coupled to a distal end of the body adjacent the distal opening, the anchor including a first anchor extending from a first side of a distal end of the body, and a second anchor extending from a second side of the distal end of the body, the second anchor separated from the first anchor; and
   a retriever comprising a pair of interconnected hooks, each hook of the pair of hooks having a first longitudinal portion extending from and unitarily formed with the wall and a second portion connected to the first longitudinal portion, the second portions of the interconnected hooks, each hook being formed of the material of the wall having the thickness.

19. The endovascular implant of item 18, wherein the body comprises a mesh.

Each of the following terms written in singular grammatical form: "a", "an", and "the", as used herein, means "at least one", or "one or more". Use of the phrase "one or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "an apparatus", "an assembly", "a mechanism", "a component, "an element", and "a step or procedure", as used herein, may also refer to, and encompass, a plurality of units, a plurality of apparatuses, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of and "consists of, as used herein, means "including and limited to". The phrase "consisting essentially of" means that the stated entity or item (system, system unit, system sub-unit apparatus, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit apparatus, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated value. Use of the terms parallel or perpendicular are meant to mean approximately meeting this condition, unless otherwise specified.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions of this disclosure have been illustratively described and presented by way of specific exemplary embodiments, and examples thereof, it is evident that many alternatives, modifications, or/and variations, thereof, will be apparent to those skilled in the art. For example, while a pair of hooks is described above, it can be appreciated that more than two hooks can be used to form the single hook, and thus retriever 18. Likewise, multiple single hooks, each formed of a double hook, can be provided on a single implant, if desired for a particular use. Accordingly, it is intended that all such alternatives, modifications, or/and variations, fall within the spirit of, and are encompassed by, the broad scope of the appended claims.

The invention claimed is:

1. An endovascular implant for forming a fistula, comprising:
   a body including a wall forming a lumen, the body including a distal end having a distal opening and a proximal end having a proximal opening; and
   an anchor coupled to a distal end of the body adjacent the distal opening, the anchor including a first anchor extending from a first side of a distal end of the body, and a second anchor extending from a second side of the distal end of the body, the second anchor separated from the first anchor; and
   a single retriever formed by a pair of interconnected hooks having a juxtaposed, abutting relationship.

2. The endovascular implant of claim 1, wherein the first and second anchors are separated by an inlet to the lumen.

3. The endovascular implant of claim 1, wherein the wall comprises a material having a thickness, each hook of the pair of hooks having a first longitudinal portion extending from and unitarily formed with the wall and a second portion connected to the first longitudinal portion, the second portions of the interconnected hooks, each hook being formed of the material of the wall having the thickness.

4. The endovascular implant of claim 3, wherein the pair of hooks are at least partially connected together by a bond.

5. The endovascular implant of claim 4, wherein the bond comprises a weld.

6. The endovascular implant of claim 3, wherein the pair of interconnected hooks include a radially innermost portion offset from a central axis of the body.

7. The endovascular implant of claim 3, wherein the first longitudinal portion of each hook is partially twisted and the second portion projects radially inward from the first longitudinal portion.

8. The endovascular implant of claim 1, wherein the body comprises a mesh having a coating.

9. The endovascular implant of claim 1, wherein the proximal end of the body is tapered.

10. An endovascular implant for forming a fistula, comprising:
    a body including a wall forming a lumen, the body including a distal end having a distal opening and a proximal end having a proximal opening; and
    an anchor coupled to the distal end of the body adjacent the distal opening,
    a retriever coupled to the proximal end of the body adjacent the proximal opening, the retriever formed by a pair of interconnected hooks having a first longitudinal portion including a partial twist.

11. The endovascular implant of claim 10, wherein the wall comprises a material having a thickness, and the first longitudinal portion extends from and is unitarily formed with the wall and a second portion connected to the first longitudinal portion, the second portions of the interconnected hooks, each hook being formed of the material of the wall having the thickness.

12. The endovascular implant of claim 11, wherein the pair of hooks are at least partially connected together by a bond.

13. The endovascular implant of claim 12, wherein the bond comprises a weld.

14. The endovascular implant of claim 11, wherein the pair of interconnected hooks include a radially innermost portion offset from a central axis of the body.

15. The endovascular implant of claim 11, wherein the second portion projects radially inward from the first longitudinal portion.

16. The endovascular implant of claim 11, wherein the body comprises a mesh having a coating.

17. The endovascular implant of claim 11, wherein the anchor comprises first and second anchors separated by an inlet to the lumen.

18. An endovascular implant for forming a fistula, comprising:
    a body including a wall forming a lumen, the body including a distal end having a distal opening and a proximal end having a proximal opening;
    an anchor coupled to a distal end of the body adjacent the distal opening, the anchor including a first anchor extending from a first side of a distal end of the body, and a second anchor extending from a second side of the distal end of the body, the second anchor separated from the first anchor; and
    a retriever comprising a pair of hooks bonded together by a weld in a juxtaposed, abutting relationship each hook of the pair of hooks having a first longitudinal portion extending from and unitarily formed with the wall and a second portion connected to the first longitudinal portion, each hook being formed of the material of the wall having the thickness.

19. The endovascular implant of claim 18, wherein the body comprises a mesh having a coating.

20. The endovascular implant of claim 18, wherein the first and second anchors are separated by an inlet to the lumen.

* * * * *